United States Patent [19]

Guala

[11] Patent Number: 5,611,576
[45] Date of Patent: Mar. 18, 1997

[54] FEMALE COUPLING ELEMENT FOR HAEMODIALYSIS MEDICAL EQUIPMENT

[75] Inventor: Ernesto Guala, Turin, Italy

[73] Assignee: Industrie Borla SpA, Turin, Italy

[21] Appl. No.: 562,452

[22] Filed: Nov. 24, 1995

[51] Int. Cl.$^6$ ................................................. F16L 35/00
[52] U.S. Cl. ........................... 285/38; 285/332; 285/393; 285/423; 285/921
[58] Field of Search ........................... 285/38, 332, 393, 285/423, 921

[56] References Cited

U.S. PATENT DOCUMENTS 4,443,028  4/1984  Hayes ................................. 285/38
4,629,455  12/1986  Kanno ............................. 285/332 X
4,639,019  1/1987  Mittleman ......................... 285/332
5,286,067  2/1994  Choksi ............................. 285/38

Primary Examiner—Dave W. Arola
Attorney, Agent, or Firm—Sughrue, Mion, Zinn, Macpeak & Seas

[57] ABSTRACT

A female coupling element of the Luer-Lock type for haemodialysis medical equipment comprises an outer tubular body made of a relatively rigid moulded thermoplastic material, and an inner sleeve made of a relatively softer moulded thermoplastic material and axially fitted within the outer body. The outer body and the inner sleeve are freely rotatable relative to each other.

2 Claims, 1 Drawing Sheet

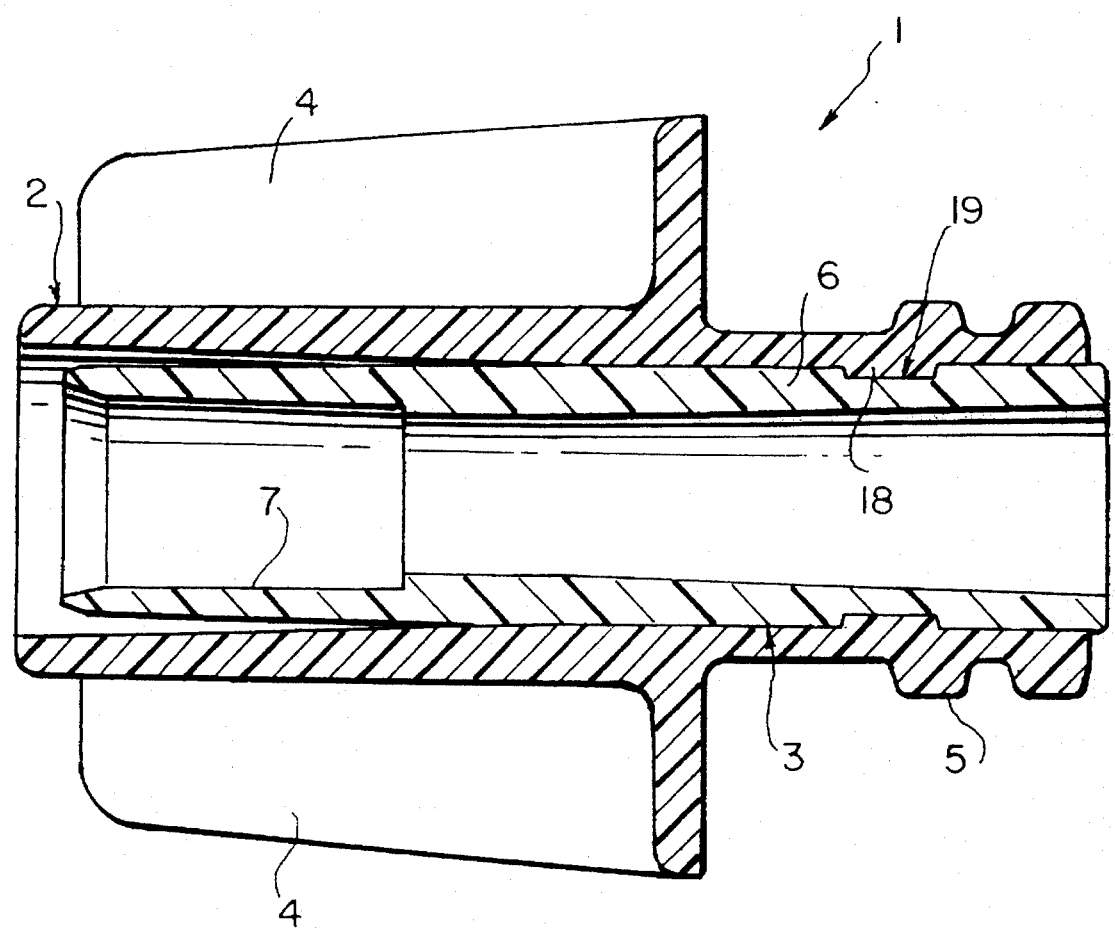

FEMALE COUPLING ELEMENT FOR HAEMODIALYSIS MEDICAL EQUIPMENT

BACKGROUND OF THE INVENTION

The present invention is related in general to connectors for haemodialysis medical equipment.

More particularly, the invention relates to a female coupling element of the Luer-Lock type, comprising an outer tubular body formed with a handgrip member and an outerly threaded portion, and an inner sleeve coaxially fitted within the outer body and defining, in correspondence of the outerly threaded portion thereof, a Luer cone for connection to a male coupling element, said inner sleeve being axially retained within the outer body and being intended to be connected, on the side opposite to the Luer cone, to a tube, bag, or the like, and wherein the outer body and the inner sleeve are made of two different moulded thermoplastic materials the first of which is relatively rigid and the second of which is relatively soft.

A female coupling element of the above referenced type is known from EP-B-0248979, according to which the outer body is provided with apertures within which complementary projections of the inner sleeve are engaged, whereby the two components are rotationally rigid with each other.

This construction involves a certain manufacturing complication and may involve difficulties upon connecting the female coupling element with the associated male coupling element, owing to rigidity of the two coupling components which may cause torsion of the tube or the like already connected (normally bonded) at the opposite side to the Luer cone.

SUMMARY OF THE INVENTION

The object of the present invention is to avoid the above drawbacks, and this object is achieved by a female coupling element of the above-referenced type, characterized in that the outer body and the inner sleeve are freely rotatable relative to each other and are axially joined therebetween by means of an inner annular projection of the former in which an outer annular groove of the latter is snap fitted.

BRIEF DESCRIPTION OF THE DRAWINGS

The invention will now be disclosed in detail with reference to the accompanying drawing purely provided by way of non-limiting example, which is a diagrammatic longitudinal section of a female coupling element according to the invention.

DESCRIPTION OF THE PREFERRED EMBODIMENT

Referring to the drawing, reference numeral 1 generally designates a female coupling element for haemodialysis medical equipment, constituted by two distinct elements, namely an outer tubular body 2 and an inner sleeve 3.

The outer tubular body 2 is formed with a pair of diametrically opposed wings 4 defining a handgrip, and with an outerly threaded portion 5.

The outer body is made of a relatively rigid moulded thermoplastic material, for instance propylene or the like.

The inner sleeve 3 is made of a softer moulded thermoplastic material, for instance PVC or the like. The inner sleeve 3 has a portion 6, extending on the same side of the threaded portion 5 of the body 2, the cavity of which has a conical surface defining a Luer cone for connection to a male coupling element, not shown in the drawing.

On the other side, the inner sleeve 3 has a cavity portion 7 intended for connection to a tube, bag or the like.

According to the invention, the inner sleeve 3 is only retained axially within the body 2, while it is freely rotatable relative to the body 2.

For axial retainment of the sleeve 3, the body 1 is provided near to the outerly threaded portion 5 with an inner annular collar 18 engaging a corresponding outer annular groove 19 of the sleeve 3. Engagement therebetween, which enables mutual rotation between the body 2 and the sleeve 3, is performed by means of a snap fitting upon axial insertion of the sleeve 3 within the body 2.

Naturally the axial retainment of the sleeve 3 relative to the body 2 may be carried out in a different way with respect to that disclosed in the example, provided that free rotation is allowed between the two components of the coupling element 1, for instance by means of a constructively different snap engagement or equivalent systems.

In use, connection between the female coupling element 1 and a complementary male coupling element is performed by means of rotation of the body 1 and screwing of the threaded portion 5 within the male coupling element, which is then locked following axial forced fitting within the Luer cone 6 defined by the inner sleeve 3. Owing to free rotation of the body 2 over the sleeve 3, this operation can be performed in a particularly convenient and easy way.

What is claimed is:

1. A female coupling element of the Luer-Lock type for haemodialysis medical equipment, comprising an outer tubular body made of a first relatively rigid thermoplastic material and having an outer surface formed with a handgrip and a threaded portion, and an inner cylindrical surface;

an inner sleeve made of a second relatively soft thermoplastic material and having an outer cylindrical surface which is coaxially and closely fitted within said inner cylindrical surface of said outer tubular body, and an inner conical surface defining a Luer connector for connection to a male coupling element;

and mutually retaining means integrally formed in said inner and outer cylindrical surfaces, respectively, for axially retaining said inner sleeve within said outer tubular body, while allowing said inner sleeve and said outer tubular body to be freely rotatable relative to each other.

2. A female coupling element according to claim 1, wherein said mutually retaining means comprise mutually snap-fitted annular projection means and annular groove means.

* * * * *